US011474129B2

(12) United States Patent
Seidman et al.

(10) Patent No.: US 11,474,129 B2
(45) Date of Patent: Oct. 18, 2022

(54) METHODS AND SYSTEMS FOR HOMOGENOUS OPTICALLY-PUMPED VAPOR CELL ARRAY ASSEMBLY FROM DISCRETE VAPOR CELLS (71) Applicant: HI LLC, Los Angeles, CA (US)

(72) Inventors: Scott Jeremy Seidman, Glenview, IL (US); Ethan Pratt, Santa Clara, CA (US); Jeffery Kang Gormley, Chatsowrth, CA (US); Dakota Blue Decker, Culver City, CA (US); Micah Ledbetter, Sunnyvale, CA (US)

(73) Assignee: HI LLC, Los Angeles, CA (US)

( * ) Notice: Subject to any disclaimer, the term of this patent is extended or adjusted under 35 U.S.C. 154(b) by 234 days.

(21) Appl. No.: 17/087,988

(22) Filed: Nov. 3, 2020

(65) Prior Publication Data
US 2021/0139742 A1 May 13, 2021

Related U.S. Application Data (60) Provisional application No. 62/971,132, filed on Feb. 6, 2020, provisional application No. 62/933,085, filed on Nov. 8, 2019.

(51) Int. Cl.
G01R 3/00 (2006.01)
C09J 163/00 (2006.01)
(Continued)

(52) U.S. Cl.
CPC .............. G01R 3/00 (2013.01); B29C 65/782 (2013.01); C09J 163/00 (2013.01);
(Continued)

(58) Field of Classification Search
CPC .............. B29C 65/782; B29C 65/7826; B29C 65/7855; B29C 65/542; G01R 33/0094; G01R 3/00
See application file for complete search history.

(56) References Cited

U.S. PATENT DOCUMENTS 3,173,082 A 3/1965 Bell et al.
3,257,608 A 6/1966 Bell et al.
(Continued)

FOREIGN PATENT DOCUMENTS

CN 104730484 6/2015
CN 107562188 1/2018
(Continued)

OTHER PUBLICATIONS

S. Woetzel et al., Microfabricated atomic vapor cell arrays for magnetic field measurements, Mar. 25, 2011, Review of Scientific Instruments 82 (Year: 2011).*
(Continued)

Primary Examiner — Scott W Dodds
(74) Attorney, Agent, or Firm — Branch Partners PLLC; Bruce E. Black (57) ABSTRACT A method of making an array of vapor cells for an array of magnetometers includes providing a plurality of separate vapor cell elements, each vapor cell element including at least one vapor cell; arranging the vapor cell elements in an alignment jig to produce a selected arrangement of the vapor cells; attaching at least one alignment-maintaining film onto the vapor cell elements in the alignment jig; transferring the vapor cells elements and the at least one alignment-maintaining film from the alignment jig to a mold; injecting a bonding material into the mold and between the vapor cell elements to bond the vapor cell elements in the selected arrangement; removing the at least one alignment maintaining film from the vapor cell elements; and removing the bonded vapor cells elements in the selected arrangement from the mold to provide the array of vapor.

20 Claims, 7 Drawing Sheets (51) Int. Cl.
   *G01R 33/032* (2006.01)
   *G01R 33/26* (2006.01)
   *B29C 65/78* (2006.01)
   *B29C 65/54* (2006.01)
   *G01R 33/00* (2006.01)

(52) U.S. Cl.
   CPC ............ *G01R 33/032* (2013.01); *G01R 33/26* (2013.01); *B29C 65/542* (2013.01); *B29C 65/7826* (2013.01); *B29C 65/7841* (2013.01); *B29C 65/7855* (2013.01); *G01R 33/0094* (2013.01)

(56) References Cited

U.S. PATENT DOCUMENTS

| | | |
|---|---|---|
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |
| 5,192,921 A | 3/1993 | Chantry et al. |
| 5,225,778 A | 7/1993 | Chaillout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keene et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okandan et al. |
| 7,872,473 B2 | 1/2011 | Kitching et al. |
| 7,994,783 B2 | 8/2011 | Ledbetter et al. |
| 3,054,074 A1 | 11/2011 | Ichihara et al. |
| 8,212,556 B1 | 7/2012 | Schwindt et al. |
| 8,258,884 B2 | 9/2012 | Borwick, III et al. |
| 8,319,156 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,084,549 B2 | 7/2015 | Desain et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Komack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Mem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Komack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,024,929 B2 | 7/2018 | Parsa et al. |
| 10,088,535 B1 | 10/2018 | Shah |
| 10,162,016 B2 | 12/2018 | Gabrys et al. |
| 10,194,865 B2 | 2/2019 | Le et al. |
| 10,314,508 B2 | 6/2019 | Desain et al. |
| 10,371,764 B2 | 8/2019 | Morales et al. |
| 10,772,561 B2 | 9/2020 | Donaldson |
| 11,313,926 B1 * | 4/2022 | Amarloo ............ G01R 33/0052 |
| 2004/0232912 A1 | 11/2004 | Tsukamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2007/0076776 A1 | 4/2007 | Lust et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0079426 A1 | 3/2009 | Anderson |
| 2009/0101806 A1 | 4/2009 | Masuda |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2012/0206135 A1 | 8/2012 | Nagasaka et al. |
| 2013/0082700 A1 | 4/2013 | Mizutani et al. |
| 2013/0082701 A1 | 4/2013 | Mizutani et al. |
| 2013/0265042 A1 | 10/2013 | Kawabata et al. |
| 2014/0121491 A1 | 5/2014 | Zhang |
| 2014/0159718 A1 | 6/2014 | Larsen et al. |
| 2014/0306700 A1 | 10/2014 | Kamada et al. |
| 2014/0354275 A1 | 12/2014 | Sheng et al. |
| 2015/0022200 A1 | 1/2015 | Ichihara et al. |
| 2015/0054504 A1 | 2/2015 | Ichihara et al. |
| 2015/0378316 A1 | 12/2015 | Parsa et al. |
| 2016/0018476 A1 | 1/2016 | Ooi et al. |
| 2016/0061913 A1 | 3/2016 | Kobayashi et al. |
| 2016/0116553 A1 | 4/2016 | Kim et al. |
| 2016/0223627 A1 | 8/2016 | Shah et al. |
| 2016/0291099 A1 | 10/2016 | Ueno |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0067969 A1 | 3/2017 | Butters et al. |
| 2017/0199138 A1 | 7/2017 | Parsa et al. |
| 2017/0199251 A1 | 7/2017 | Fujii et al. |
| 2017/0261564 A1 | 9/2017 | Gabrys et al. |
| 2017/0331485 A1 | 11/2017 | Gobet et al. |
| 2017/0343617 A1 | 11/2017 | Manickam et al. |
| 2017/0343695 A1 | 11/2017 | Stetson et al. |
| 2017/0356969 A1 | 12/2017 | Ueno |
| 2017/0360322 A1 | 12/2017 | Ueno |
| 2017/0363695 A1 | 12/2017 | Ueno |
| 2018/0003777 A1 | 1/2018 | Sorenson et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |
| 2018/0372813 A1 | 12/2018 | Bulatowicz et al. |
| 2019/0154769 A1 | 5/2019 | Nagasaka et al. |
| 2019/0391213 A1 | 12/2019 | Mford |
| 2020/0025844 A1 | 1/2020 | Alford et al. |

(56) References Cited

U.S. PATENT DOCUMENTS

| | | |
|---|---|---|
| 2020/0057115 A1 | 2/2020 | Jiménez-Martínez et al. |
| 2020/0057116 A1 | 2/2020 | Zorzos et al. |
| 2020/0064421 A1 | 2/2020 | Kobayashi et al. |
| 2020/0072916 A1 | 3/2020 | Alford et al. |
| 2020/0088811 A1 | 3/2020 | Mohseni |
| 2020/0241094 A1 | 7/2020 | Alford |
| 2020/0256929 A1 | 8/2020 | Ledbetter et al. |
| 2020/0309873 A1 | 10/2020 | Ledbetter et al. |
| 2020/0334559 A1 | 10/2020 | Anderson et al. |
| 2020/0341081 A1 | 10/2020 | Mohseni et al. |
| 2020/0381128 A1 | 12/2020 | Pratt et al. |
| 2020/0400763 A1 | 12/2020 | Pratt |
| 2021/0011094 A1 | 1/2021 | Bednarke |
| 2021/0015385 A1 | 1/2021 | Katnani et al. |
| 2021/0015427 A1 | 1/2021 | Shah et al. |
| 2021/0041512 A1 | 2/2021 | Pratt et al. |
| 2021/0041513 A1 | 2/2021 | Mohseni |
| 2021/0063510 A1 | 3/2021 | Ledbetter |
| 2021/0114926 A1* | 4/2021 | Ramirez-Serrano ................ G01R 29/0864 |

FOREIGN PATENT DOCUMENTS

| | | |
|---|---|---|
| CN | 110742607 | 2/2020 |
| CN | 110859610 | 3/2020 |
| DE | 102016114542 | 2/2018 |
| EP | 2738627 A3 | 6/2014 |
| EP | 2380029 B1 | 10/2015 |
| EP | 3037836 B1 | 9/2017 |
| JP | 2016109665 | 6/2016 |
| JP | 2018004462 | 1/2018 |
| WO | 2005/081794 | 9/2005 |
| WO | 2014/031985 | 2/2014 |
| WO | 2017/095998 | 6/2017 |
| WO | 2020/084194 | 4/2020 |

OTHER PUBLICATIONS

Zhang Xin et al: "Detection and analysis of MEG signals in occipital region with double-channel OPM sensors", Journal of Neuroscience Methods, Elsevier Science Publisher B. V., Amsterdam, NL, vol. 346, Sep. 17, 2020 (Sep. 17, 2020).

Okada, Y.C., Lahteenmäki, A. and Xu, C., "Experimental analysis of distortion of magnetoencephalography signals by the skull." Clinical neurophysiology 110 (2), 230-238 (1999).

Robinson, J.T., Pohlmeyer, E., Gather, M.C., Kemere, C., Kitching, J.E., Malliaras, G.G., Marblestone, A., Shepard, K. L., Stieglitz, T. and Xie, C., "Developing Next-Generation Brain Sensing Technologies—A Review." IEEE sensors journal, 19(22), 10163-10175 (2019).

Shah, V., Knappe, S., Schwindt, P.D. and Kitching, J., "Subpicotesla atomic magnetometry with a microfabricated vapour cell." Nature Photon 1, 649-652 (2007).

Griffith, W.C., Knappe, S. and Kitching, J., "Femtotesla atomic magnetometry in a microfabricated vapor cell." Optics express 18, (26), 27167-27172 (2010).

Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multi-channel magnetoencephalography." NeuroImage, 199, 598-608 (2019).

Iivanainen, J., Zetter, R , Grön, M , Hakkarainen, K and Parkkonen, L., "On-scalp MEG system utilizing an actively shielded array of optically-pumped magnetometers." Neuroimage 194, 244-258 (2019).

Iivanainen, J., Stenroos, M. and Parkkonen, L., "Measuring MEG closer to the brain: Performance of on-scalp sensor arrays." NeuroImage 147, 542-553 (2017).

Kitching, J., Knappe, S , Gerginov, V., Shah, V., Schwindt, P.D., Lindseth, B., Donley E.A., "Chip-scale atomic devices: precision atomic instruments based on MEMS." In Frequency Standards and Metrology, 445-453 (2009).

Kitching, J., Knappe, S. and Donley, E.A., "Atomic sensors—a review." IEEE Sensors Journal, 11(9), 1749-1758 (2011).

Budker, D. and Romalis, M., "Optical magnetometry". Nature physics, 3(4), 227-234 (2007).

Happer, W., "Optical pumping", Rev. Mod. Phys., 44 (2), 169-249 (1972).

Purcell, E.M., Field, G.B., "Influence of collisions upon population of hyperfine states in hydrogen", Astrophys. J., 124, 542 (1956).

Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).

Bloom, A. L., "Principles of operation of the rubidium vapor magnetometer." Applied Optics 1(1), 61-68 (1962).

Bell, W.E., and Bloom, A.L., "Optically driven spin precession." Physical Review Letters 6, (6), 280 (1961).

Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).

Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).

De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).

Mellinger, J., Schalk, G., Braun, C., Preissl, H., Rosenstiel, W., Birbaumer, N. and Kübler, A., "An MEG-based brain-computer interface (BCI)." Neuroimage, 36(3), 581-593 (2007).

Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).

Lightfoot, G., "Summary of the N1-P2 cortical auditory evoked potential to estimate the auditory threshold in adults". Seminars in hearing, 37(1), 1 (2016).

Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298 (1998).

Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).

Boma, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).

Hill RM, Boto E, Holmes N, et al. A tool for functional brain imaging with lifespan compliance [published correction appears in Nat Commun. Dec. 4, 2019;10(1):5628], Nat Commun. 2019;10(1):4785. Published Nov. 5, 2019. doi:10.1038/s41467-019-12486-x.

Zetter, R., Iivanainen, J. & Parkkonen, L. Optical Co-registration of MRI and On-scalp MEG. Sci Rep 9, 5490 (2019). https://doi.org/10.1038/s41598-019-41763-4.

Garrido-Jurado, Sergio, Rafael Muñoz-Salinas, Francisco José Madrid-Cuevas and Manuel J. Marín-Jiménez. "Automatic generation and detection of highly reliable fiducial markers under occlusion." Pattern Recognit. 47 (2014): 2280-2292.

Hill RM, Boto E, Rea M, et al. Multi-channel whole-head OPM-MEG: Helmet design and a comparison with a conventional system [published online ahead of print, May 29, 2020]. Neuroimage. 2020;219:116995. doi: 10.1016/j.neuroimage.2020.116995.

V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/CVPR.2014.241.

Holmes, N., Tierney, T.M., Leggett, J. et al. Balanced, bi-planar magnetic field and field gradient coils for field compensation in wearable magnetoencephalography. Sci Rep 9, 14196 (2019).

N. Holmes, J. Leggett, E. Boto, G. Roberts, R.M. Hill, T.M. Tierney, V. Shah, G.R. Barnes, M.J. Brookes, R. Bowtell A bi-planarcoil (56) References Cited

OTHER PUBLICATIONS system for nulling background magnetic fields in scalp mounted magnetoencephalography Neuroimage, 181 (2018), pp. 760-774.

J. M. Leger et al., In-flight performance of the Absolute Scalar Magnetometer vector mode on board the Swarm satellites, Earth, Planets, and Space (2015) 67:57.

Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.

Gravrand, O., Khokhlov, A., & JL, L. M. (2001). On the calibration of a vectorial 4He pumped magnetometer. Earth, planets and space , 53 (10), 949-958.

Borna, Amir & Carter, Tony & Colombo, Anthony & Jau, Y-Y & McKay, Jim & Weisend, Michael & Taulu, Samu & Stephen, Julia & Schwindt, Peter. (2018). Non-Invasive Functional-Brain-Imaging with a Novel Magnetoencephalography System. 9 Pages.

Vrba J, Robinson SE. Signal processing in magnetoencephalography. Methods. 2001;25(2):249-271. doi:10.1006/meth.2001.1238.

Uusitalo M and Ilmoniemi R., 1997, Signal-space projection method for separating MEG or EEG into components Med. Biol. Comput. (35) 135-140.

Taulu S and Kajola M., 2005, Presentation of electromagnetic multichannel data: the signal space separation method. J. Appl. Phys. (97) 124905 (2005).

Taulu S, Simola J and Kajola M., 2005, Applications of the signal space separation method. IEEE Trans. Signal Process. (53) 3359-3372 (2005).

Taulu S, Simola J., 2006, Spatiotemporal signal space separation method for rejecting nearby interference in MEG measurements. Phys. Med Biol. (51) 1759-1768 (2006).

Johnson, et al., Magnetoencephalography with a two-color pump-probe, fiber-coupled atomic magnetometer, Applied Physics Letters 97, 243703 2010.

Zhang, et al., Magnetoencephalography using a compact multichannel atomic magnetometer with pump-probe configuration, AIP Advances 8, 125028 (2018).

Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.

Ilmoniemi, R. (2009). The triangle phantom in magnetoencephalography. In 24th Annual Meeting of Japan Biomagnetism and Bioelecctromagnetics Society, Kanazawa, Japan, 28.29.5.2009 (pp. 6263).

Oyama D. Dry phantom for magnetoencephalography—Configuration, calibration, and contribution. J Neurosci Methods. 2015;251:24-36. doi: 0.1016/j.jneumeth.2015.05.004.

Chutani, R., Maurice, V., Passilly, N. et al. Laser light routing in an elongated micromachined vapor cell with diffraction gratings for atomic clock applications. Sci Rep 5, 14001 (2015). https://doi.org/10.1038/srep14001.

Eklund, E. Jesper, Andrei M. Shkel, Svenja Knappe, Elizabeth A. Donley and John Kitching. "Glass-blown spherical microcells for chip-scale atomic devices." (2008).

Jiménez-Martínez R, Kennedy DJ, Rosenbluh M, et al. Optical hyperpolarization and NMR detection of 129Xe on a microfluidic chip. Nat Commun. 2014;5:3908. Published May 20, 2014. doi:10.1038/ncomms4908.

Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.

Bruno, A. C., and P. Costa Ribeiro. "Spatial Fourier Calibration Method for Multichannel SQUID Magnetometers." Review of Scientific Instruments 62, No. 4 (Apr. 1, 1991): 1005-9.

Chella, Federico, Filippo Zappasodi, Laura Marzetti, Stefania Della Penna, and Vittorio Pizzella. "Calibration of a Multichannel MEG System Based on the Signal Space Separation Method." Physics in Medicine and Biology 57 (Jul. 13, 2012): 4855-70.

Pasquarelli, A, M De Melis, Laura Marzetti, Hans-Peter Muller, and S N Emé. "Calibration of a Vector-MEG Helmet System." Neurology & Clinical Neurophysiology☐: NCN 2004 (Feb. 1, 2004): 94.

Pfeiffer, Christoph, Lau M. Andersen, Daniel Lundqvist, Matti Hämäläinen, Justin F. Schneiderman, and Robert Oostenveld. "Localizing On-Scalp MEG Sensors Using an Array of Magnetic Dipole Coils." Plos One 13, No. 5 (May 10, 2018): e0191111.

Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.

Nagel, S., & Spüler, M. (2019). Asynchronous non-invasive high-speed BCI speller with robust non-control state detection. Scientific Reports, 9(1), 8269.

Thielen, J., van den Broek, P., Farquhar, J., & Desain, P. (2015). Broad-Band Visually Evoked Potentials: Re(con) volution in Brain-Computer Interfacing. PloS One, 10(7), e0133797. https://doi.org/10.1371/journal.pone.0133797.

J. Kitching, "Chip-scale atomic devices," Appl. Phys. Rev. 5(3), 031302 (2018), 39 pages.

Arjen Stolk, Ana Todorovic, Jan-Mathijs Schoffelen, and Robert Oostenveld. "Online and offline tools for head movement compensation in MEG." Neuroimage 68 (2013): 39-48.

Bagherzadeh, Yasaman, Daniel Baldauf, Dimitrios Pantazis, and Robert Desimone. "Alpha synchrony and the neurofeedback control of spatial attention." Neuron 105, No. 3 (2020): 577-587.

Rui Zhang, Rahul Mhaskar, Ken Smith, Easswar Balasubramaniam, Mark Prouty. "All Optical Scalar Atomic Magnetometer Capable of Vector Measurement," Submitted on Nov. 17, 2020. https://arxiv.org/abs/2011.08943; Geometrics, Inc., San Jose, CA, 95131, USA.

Pyragius, T., Marin Florez, H., & Fernholz, T. (2019). A Voigt effect based 3D vector magnetometer. Physical Review A, 100(2), https://doi.org/10.1103/PhysRevA.100.023416.

Allred, J. C., Lyman, R. N., Kornack, T. W., & Romalis, M. V. (2002). High-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Boma, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

Dang, H.B. & Maloof, A.C. & Romalis, Michael (2009) Ultra-high sensitivity magnetic field and magnetization measurements with an atomic magnetometer. Applied Physics Letters. 97. 10.1063/1.3491215.

Donley, E.A. & Hodby, E & Hollberg, L & Kitching, J. (2007) Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics vol. 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell Physical Review Applied (10).ISSN 2331-7019.

Jiménez-Martínez, R., Griffilh, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.

Kiwoong Kim, Sarno Begus, Hui Xia, Seung-Kyun Lee, Vojko Jazbinsek, Zvonko Trontelj, Michael V. Romalis, Multi-channel (56) References Cited

OTHER PUBLICATIONS atomic magnetometer for magnetoencephalography: A configuration study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999.10.1007/978-3-642-33045-2_49.

Kominis, I.K., Komack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi: 10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84.10.1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer Biomed Opt Express. 2012;3(5):981-90.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, S. J., and Romalis, M.V., "Unshielded three-axis vector operation of a spin-exchange-relaxation-free atomic magnetometer." Applied physics letters 85.20 (2004): 4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters 110. 10.1063/1.4974349.

Sheng, Dehong & Li, S & Dural, Nezih & Romalis, Michael. (2013). Subfemtotesla Scalar Atomic Magnetometry Using Multipass Cells. Physical review letters. 110. 160802.10.1103/PhysRevLett.110.160802.

Volkmar Schultze et al. An Optically Pumped Magnetometer Working in the Light-Shift Dispersed Mz Mode, Sensors 2017, 17, 561; doi: 10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.

Griflith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports. 6. 24773 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martínez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).

Slocum et al., Self-Calibrating Vector Magnetometer for Space, https://esto.nasa.gov/conferences/estc-2002/Papers/B3P4(Slocum).pdf.

Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0375-9601(69)90480-0.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

Borna, Amir, et al. "A 20-channel magnetoencephalography system based on optically pumped magnetometers." Physics in Medicine & Biology 62.23 (2017): 8909.

R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically bumped magnetometer. Applied Optics. 56. 5927. 10.1364/AO.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

A.B. Baranga et al., An atomic magnetometer for brain activity imaging, Real Time Conference 2005. 14th IEEE-NPSS. pp. 417-418.

Larry J. Ryan, Robert E. Slocum, and Robert B. Steves, Miniature Vector Laser Magnetometer Measurements of Earth's Field, May 10, 2004, 4 pgs.

Lorenz, V. O., Dai, X., Green, H., Asnicar, T. R., & Cundiff, S. T. (2008). High-density, high-temperature alkali vapor cell. Review of Scientific Instruments, 79(12), 4 pages.

F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.

Huang, Haichao, et al. "Single-beam three-axis atomic magnetometer." Applied Physics Letters 109.6 (2016): 062404. (Year: 2016).

Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.

Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2018), pp. 186-189.

Boto, E, Holmes, N, Leggett, J, Roberts, G, Shah, V, Meyer, SS, Muñoz, LD, Mullinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.

Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.

Tierney, T. M., Holmes, N., Meyer, S. S., Boto, E., Roberts, G., Leggett, J., . . . Barnes, G. R. (2018). Cognitive neuroscience using (56) References Cited

OTHER PUBLICATIONS wearable magnetometer arrays: Non-invasive assessment of language function. NeuroImage, 181, 513-520.

Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.

International Search Report and Written Opinion for PCT Application No. PCT/US2020/058663 dated Feb. 22, 2021.

* cited by examiner

METHODS AND SYSTEMS FOR HOMOGENOUS OPTICALLY-PUMPED VAPOR CELL ARRAY ASSEMBLY FROM DISCRETE VAPOR CELLS

CROSS-REFERENCE TO RELATED APPLICATIONS

This application claims the benefit of U.S. Provisional Patent Applications Ser. Nos. 62/933,085, filed Nov. 8, 2019, and 62/971,132, filed Feb. 6, 2020, both of which are incorporated herein by reference in their entireties.

FIELD

The present disclosure is directed to the area of magnetic field measurement systems including systems for magnetoencephalography (MEG). The present disclosure is also directed to methods and systems for manufacturing an array of vapor cells for a magnetic field measurement system.

BACKGROUND

In the nervous system, neurons propagate signals via action potentials. These are brief electric currents which flow down the length of a neuron causing chemical transmitters to be released at a synapse. The time-varying electrical currents within an ensemble of neurons generates a magnetic field. Magnetoencephalography (MEG), the measurement of magnetic fields generated by the brain, is one method for observing these neural signals.

Existing technology for measuring MEG typically utilizes superconducting quantum interference devices (SQUIDs) or collections of discrete optically pumped magnetometers (OPMs). SQUIDs require cryogenic cooling, which is bulky, expensive, and requires a lot of maintenance. These requirements preclude their application to mobile or wearable devices.

An alternative to an array of SQUIDs is an array of OPMs. For MEG and other applications, the array of OPMs may have a large number of OPM sensors that are tightly packed. Such dense arrays can produce a high resolution spatial mapping of the magnetic field, and at a very high sensitivity level. Such OPM sensors can be used for a wide range of applications, including sensing magnetic fields generated by neural activities, similar to MEG systems.

BRIEF SUMMARY

One embodiment is a method of making an array of vapor cells for an array of magnetometers. The method includes providing a plurality of separate vapor cell elements, each vapor cell element including at least one vapor cell; arranging the vapor cell elements in an alignment jig to produce a selected arrangement of the vapor cells; attaching at least one alignment-maintaining film onto the vapor cell elements in the alignment jig; transferring the vapor cells elements and the at least one alignment-maintaining film from the alignment jig to a mold; injecting a bonding material into the mold and between the vapor cell elements to bond the vapor cell elements in the selected arrangement; removing the at least one alignment maintaining film from the vapor cell elements; and removing the bonded vapor cells elements in the selected arrangement from the mold to provide the array of vapor cells.

In at least some embodiments, at least one of the vapor cell elements includes multiple vapor cells. In at least some embodiments, the alignment jig includes a plurality of spacing features to separate the vapor cell elements in the selected arrangement. In at least some embodiments, each of the spacing features provides a same separation distance between the vapor cell elements separated by the spacing features. In at least some embodiments, at least two of the spacing features provide a different separation distance between the vapor cell elements separated by those spacing features. In at least some embodiments, the spacing features include partially drafted faces to facilitate insertion of the vapor cell elements. In at least some embodiments, the spacing features have a width that is thinner than a final separation distance between the vapor cell elements separated by the spacing features.

In at least some embodiments, attaching the at least one alignment-maintaining film includes attaching a first alignment-maintaining film onto the vapor cell elements in the alignment jig and then attaching a second alignment-maintaining film on an opposite side of the vapor cell elements from the first alignment-maintaining film. In at least some embodiments, the method further includes removing the vapor cell elements from the alignment jig prior to attaching the second alignment-maintaining film.

In at least some embodiments, the bonding material is epoxy. In at least some embodiments, the bonding material is a thermally conductive epoxy. In at least some embodiments, the bonding material is a flexible epoxy.

In at least some embodiments, the selected arrangement includes different spacing between at least two pairs of adjacent vapor cell elements. In at least some embodiments, the selected arrangement includes an irregular arrangement of the vapor cell elements. In at least some embodiments, the selected arrangement includes at least one of the vapor cell elements raised or lowered relative to an adjacent one of the vapor cell arrangements. In at least some embodiments, the selected arrangement includes at least one of the vapor cells having a different size from another one of the vapor cells. In at least some embodiments, each of the vapor cells includes optical windows, wherein the selected arrangement includes at least one of the vapor cells having a different orientation of the optical windows from another one of the vapor cells.

In at least some embodiments, the method further includes locating an alkali metal droplet in a specified location in each of the vapor cells. In at least some embodiments, locating the alkali metal droplet includes controlling a temperature of the array of vapor cells to locate the alkali metal droplets in the specified locations. In at least some embodiments, controlling the temperature includes applying a temperature gradient to the array of vapor cells to locate the alkali metal droplets in the specified locations.

Another embodiment is an array of vapor cells made by any of the methods described above. Yet another embodiment is an array of magnetometers formed from the array of vapor cells. A further embodiment is a magnetic field measurement system including the array of magnetometers.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of magnetic field measurement systems including systems for magnetoencephalography (MEG). The present disclosure is also directed to methods and systems for manufacturing an array of vapor cells for a magnetic field measurement system.

Herein the terms "ambient background magnetic field" and "background magnetic field" are interchangeable and used to identify the magnetic field or fields associated with sources other than the magnetic field measurement system and the magnetic field sources of interest, such as biological source(s) (for example, neural signals from a user's brain) or non-biological source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a gas cell containing alkali metal vapor is described, but it will be recognized that other gas cells can contain different gases or vapors for operation.

The methods and systems are described herein using optically pumped magnetometers (OPMs). While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems, such as a MEG system, described herein can be used to measure or observe electromagnetic signals generated by one or more magnetic field sources (for example, neural signals or other biological sources) of interest. The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. In at least some embodiments, the system can be a wearable MEG system that can be portable and used outside a magnetically shielded room. In at least some embodiments, the system can be a wearable MEG system that can be used in a magnetically shielded room with small compensation coils around the OPM, as described in magnetic field measurement systems or methods described in U.S. Patent Applications Ser. No. 62/983,406, incorporated herein by reference in its entirety. A wearable MEG system will be used to exemplify the magnetic field measurement systems and calibration arrangements described herein; however, it will be recognized the calibration arrangements and methods described herein can be applied to other magnetic field measurement systems.

Figure 1A:
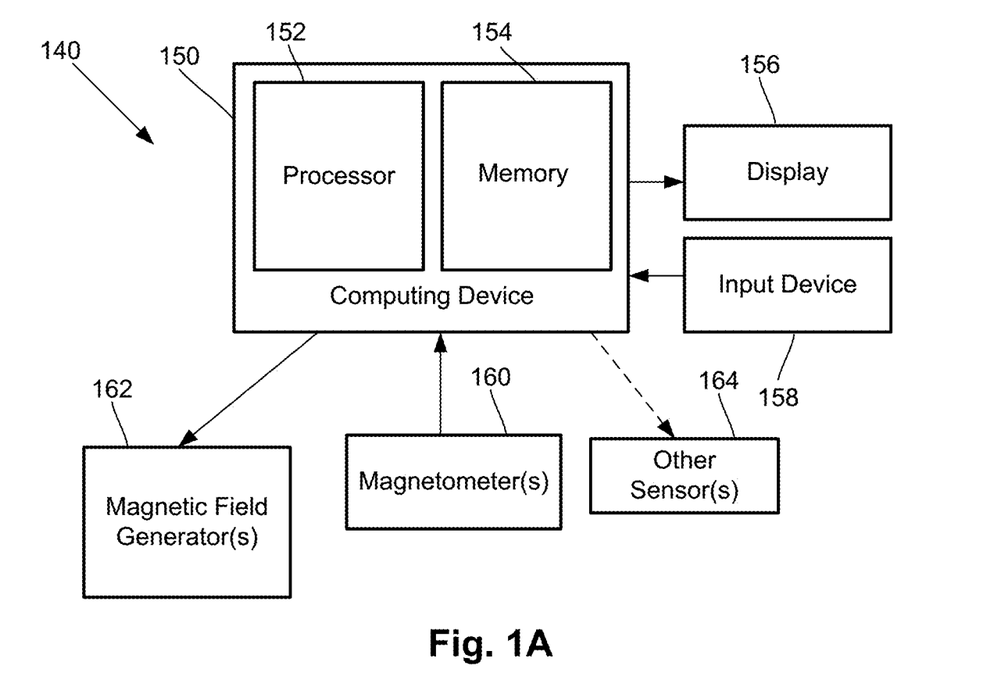
FIG. 1A is a schematic block diagram of one embodiment of a magnetic field measurement system, according to the invention.

A magnetic field measurement system, such as a MEG system, can utilize one or more magnetic field sensors. Magnetometers will be used herein as an example of magnetic field sensors, but other magnetic field sensors may also be used in addition to, or as an alternative to, the magnetometers. FIG. 1A is a block diagram of components of one embodiment of a magnetic field measurement system 140 (such as a biological signal detection system.) The system 140 can include a computing device 150 or any other similar device that includes a processor 152, a memory 154, a display 156, an input device 158, one or more magnetometers 160 (for example, an array of magnetometers) which can be OPMs, one or more magnetic field generators 162, and, optionally, one or more other sensors 164 (e.g., non-magnetic field sensors). The system 140 and its use and operation will be described herein with respect to the measurement of neural signals arising from one or more magnetic field sources of interest in the brain of a user as an example. It will be understood, however, that the system can be adapted and used to measure signals from other magnetic field sources of interest including, but not limited to, other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions stored in the memory 154.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangement can also be used. The optional sensor(s) 164 can include, but are not limited to, one or more position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode.

Figure 1B:
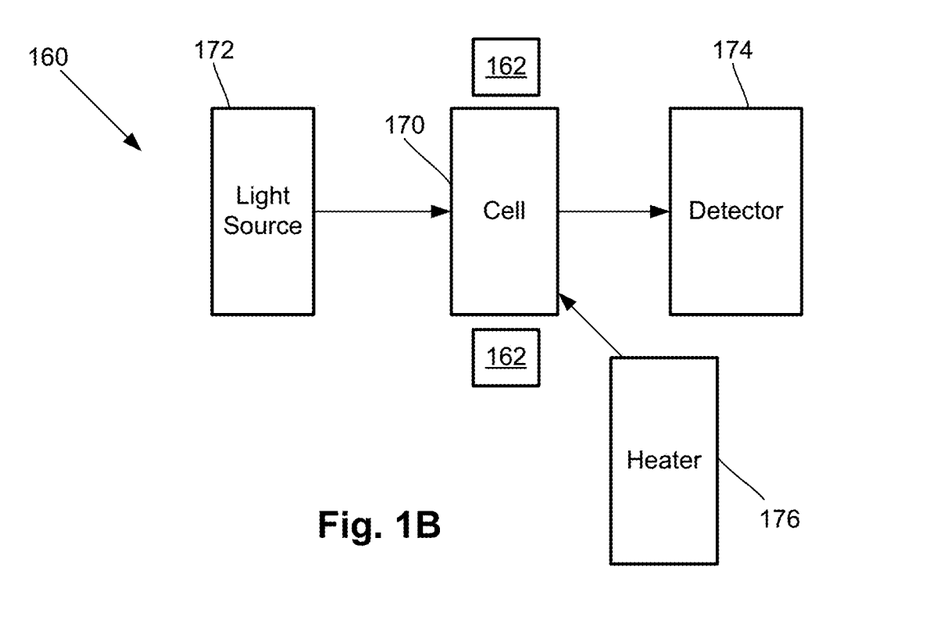
FIG. 1B is a schematic block diagram of one embodiment of a magnetometer, according to the invention.

FIG. 1B is a schematic block diagram of one embodiment of a magnetometer 160 which includes a vapor cell 170 (also referred to as a "cell") such as an alkali metal vapor cell; a heating device 176 to heat the cell 170; a light source 172; and a detector 174. In addition, coils of a magnetic field generator 162 can be positioned around the vapor cell 170. The vapor cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) and a buffer gas (for example, nitrogen, helium, neon, or argon). In some embodiments, the vapor cell may include the alkali metal atoms in a prevaporized form prior to heating to generate the vapor.

The light source 172 can include, for example, a laser to, respectively, optically pump the alkali metal atoms and probe the vapor cell. The light source 172 may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source 172 may include two light sources: a pump light source and a probe light source.

The detector 174 can include, for example, an optical detector to measure the optical properties of the transmitted probe light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
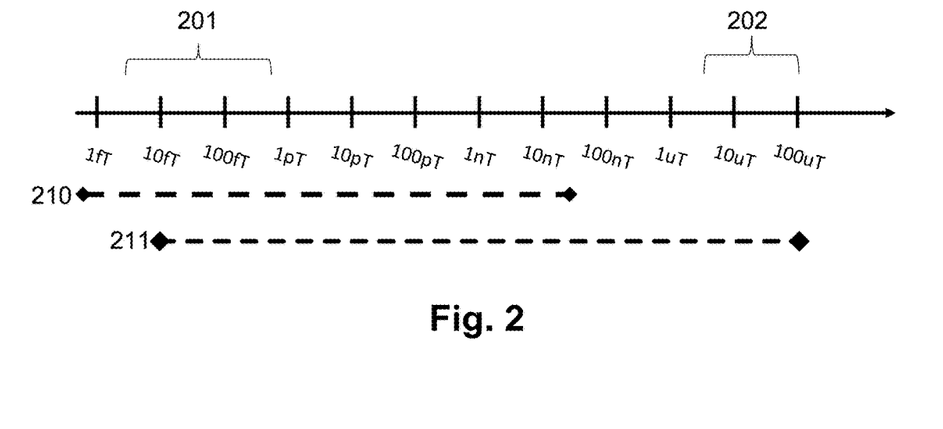
FIG. 2 shows a magnetic spectrum with lines indicating dynamic ranges of magnetometers operating in different modes.

FIG. 2 shows the magnetic spectrum from 1 fT to 100 μT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer, but many conventional SERF magnetometers typically only operate up to about 0 to 200 nT while the scalar magnetometer starts in the 10 to 100 fT range but extends above 10 to 100 µT.

A magnetic field detection system can include an array of vapor cells to form an array of magnetometers. The array may be arranged in rows and columns or can have an irregular arrangement. The array can have an overall shape that is rectangular, square, triangular, circular, oval, or any other regular or irregular shape. In at least some embodiments, the array can have vapor cells or magnetometers that are identical. In other embodiments, two or more of the vapor cells or magnetometers differ in at least one characteristic such as, but not limited to, physical dimension, vapor concentration, type of atoms in the vapor, operating temperature, coating of optical surfaces, location of alkali metal droplet condensation, or the like or any combination thereof. In at least some embodiments, an array of optically-pumped magnetometers allows gradiometric operation of single magnetometers within the array, that can be made sufficiently sensitive for background noise subtraction and neural activity recording.

Some conventional arrangements utilize single large-area vapor cells, in which gradiometry can be realized by separated optical beams through the same window. One drawback for such conventional arrangements is that the form factor of a large vapor cell may not be sufficiently flexible for use in different magnetometer architectures.

Other conventional arrangements utilize an array of individual vapor cells, each having its own window, diced in a block shape from a wafer. Drawbacks for such conventional arrangements can include form factor limitations on the block from the dicing process and decreasing yield as the number of vapor cells increases.

Yet other conventional arrangements utilize separated magnetometer systems with thermal packaging around individual vapor cells so that gradiometry is enabled by independent single magnetometers.

Some conventional mass-manufacturing methods for producing vapor cells utilize known wafer-scale fabrication of silicon cavities sealed by glass sheets. An array of vapor cells can be implemented by dicing on a pattern large enough to include two or more cell regions within one device. A risk of such approach is that a defect in any single cell region within the device pattern may render the entire device defective.

In contrast, as described herein, a vapor cell array can be created from individually diced vapor cell elements—that is, vapor cell elements formed from a dicing pattern enclosing one vapor cell or two or more (for example, two, four, six, eight, or more) vapor cells per vapor cell element. Thus, a defect-free array can be constructed from known-good vapor cells selected from a possibly imperfect wafer. In at least some embodiments, this process also allows thermal properties of the mold-assembled array to be tuned for particular system performance goals. In at least some embodiments, this process allows flexibility in the array configuration, layout, and pitch of the constitutive vapor cells in an array, without creating a new mask or wafer.

In at least some embodiments, the array can be constructed with vapor cells arranged at angles not possible (or at least difficult) to create using standard top-down wafer-scale fabrication. In at least some embodiments, this enables, for example, an array based on mass-manufacturable vapor cells, yet with optical beam directions not parallel to one another, which may be substantially beneficial, or even necessary, for sensing of magnetic fields in three dimensions.

Figure 3A:
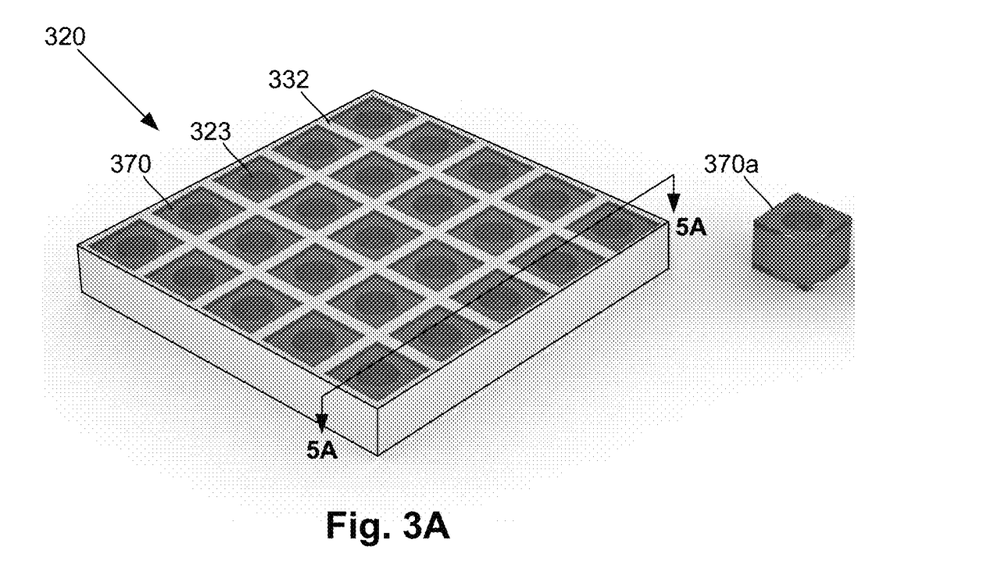
FIG. 3A is a schematic perspective view of one embodiment of an array of vapor cell elements/vapor cells and an individual vapor cell element/vapor cell, according to the invention.
Figure 4:
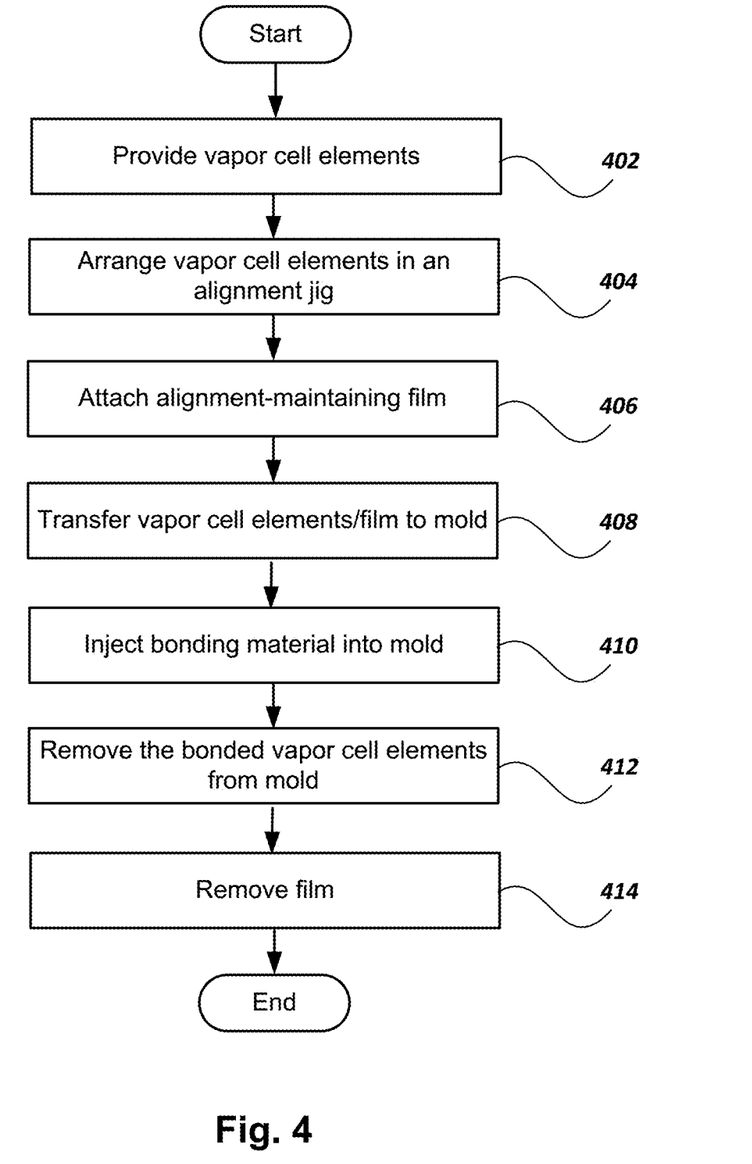
FIG. 4 is a flowchart of one embodiment of a method of making an array of vapor cells, according to the invention.

FIG. 3A illustrates one embodiment of an array 320 of vapor cell elements 370 or vapor cells, as well as an individual vapor cell element 370a or vapor cell. One embodiment of a process of forming an array of vapor cells is presented in the flow chart of FIG. 4. Step 402 includes providing the vapor cell elements 370, where each vapor cell element can include a single vapor cell or can include multiple vapor cells (for example, two, four, six, eight or more vapor cells.) This may include inspection and selection of two or more (for example, 25 vapor cells in a 5×5 array) individual vapor cell elements 370 for integration into the final vapor cell array assembly.

Figure 3B:
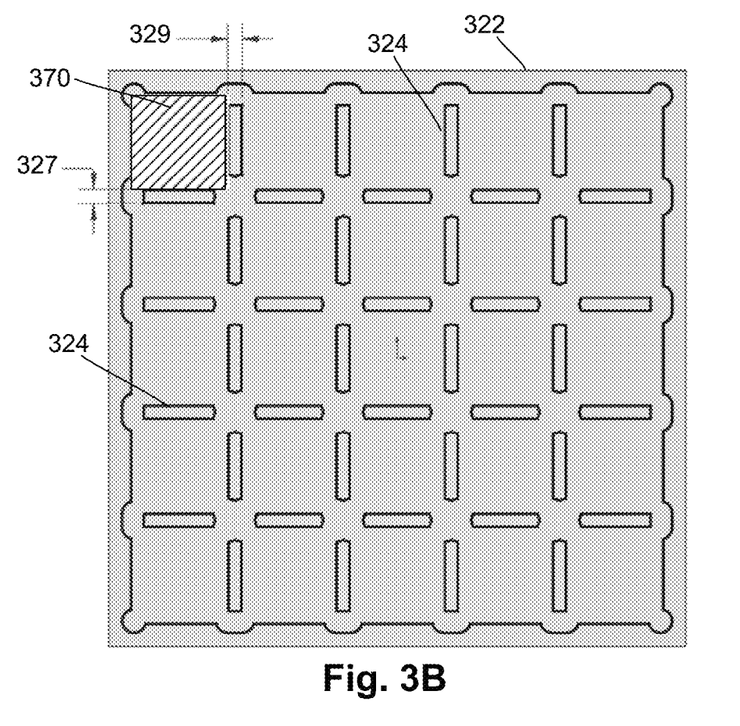
FIG. 3B is a top side view of one embodiment of an alignment jig, according to the invention.

In step 404, the vapor cell elements 370 are then set to their final pitch using an alignment jig 322 as illustrated in FIG. 3B. The alignment jig 322 can include spacing features 324 for spacing the vapor cells 370 apart from each other to give vertical spacing 327 and horizontal spacing 329 which may be the same or different. In at least some embodiments, the vertical spacing 327 can be different between different vapor cells or vapor cell elements 370. In at least some embodiments, the horizontal spacing 329 can be different between different vapor cells or vapor cell elements 370. The illustrated array is regular, but it will be understood that any other regular or irregular array can be formed using an appropriate designed alignment jig 322 which may also provide variation in a third dimension by raising or lowering vapor cells 370 relative to other vapor cells. In at least some embodiments, optical windows 323 can be arranged in the same orientation for all of the vapor cells, as illustrated in FIG. 3A. In other embodiments, the optical windows 323 of at least one of the vapor cells is oriented differently from the optical windows of another one of the vapor cells. For example, the optical windows 323 of at least one vapor cell can be oriented along one axis (for example, a z axis) and the optical windows of at least one vapor cell can be oriented along another axis (for example, a y axis) perpendicular to the first axis. There may be two, three, four, or more different orientations of the optical windows 323.

As an example, a pitch-setting alignment jig 322 can be 3D-printed using glass-filled photosensitive acrylic resin for high dimensional stability and feature accuracy. Any other suitable method of forming the alignment jig 322 can also be used. The alignment jig 322 incorporates spacing features 324 which can take the form of, for example, an array of interior ribs with partially drafted faces to help ease insertion of the vapor cell elements 370 without damaging their optical faces or silicon side walls. The width of the spacing features 324 is what sets the pitch of the vapor cell elements 370 within the final assembled array. In at least some embodiments, the width of the spacing features 324 is slightly thinner than the final pitch desired to accommodate fabrication tolerances of the alignment jig 322 and vapor cell elements 370.

Figure 3C:
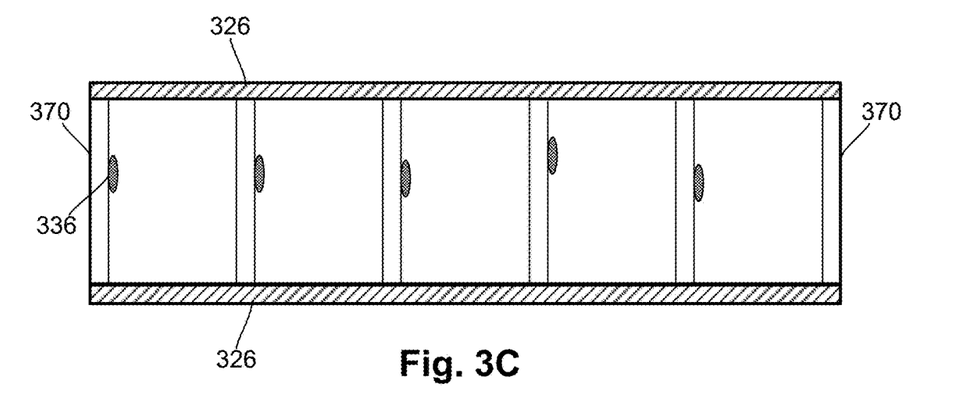
FIG. 3C is a schematic cross-sectional view of one embodiment of a row of vapor cell elements/vapor cells with two alignment-maintaining films on top and bottom, according to the invention.

In step 406, the vapor cells 370 can be locked into their relative positions by, for example, applying a suitable alignment-maintaining film 326, such as an adhesive-backed polyimide film, across exposed faces of the vapor cell elements 370, as illustrated in FIG. 3C. For example, the alignment-maintaining film 326 can be positioned on one side of the vapor cell elements 370 or on two opposing sides of the vapor cell elements, as illustrated in FIG. 3C. If applying two alignment-maintaining films 326, the first alignment-maintaining film can be added with the vapor cell elements 370 in the alignment jig 322. The second alignment-maintaining film 326 is added after the vapor cell elements 370 are removed from the alignment jig 322. Any other suitable alignment-maintaining component can be used instead of the film 326.

Figure 3D:
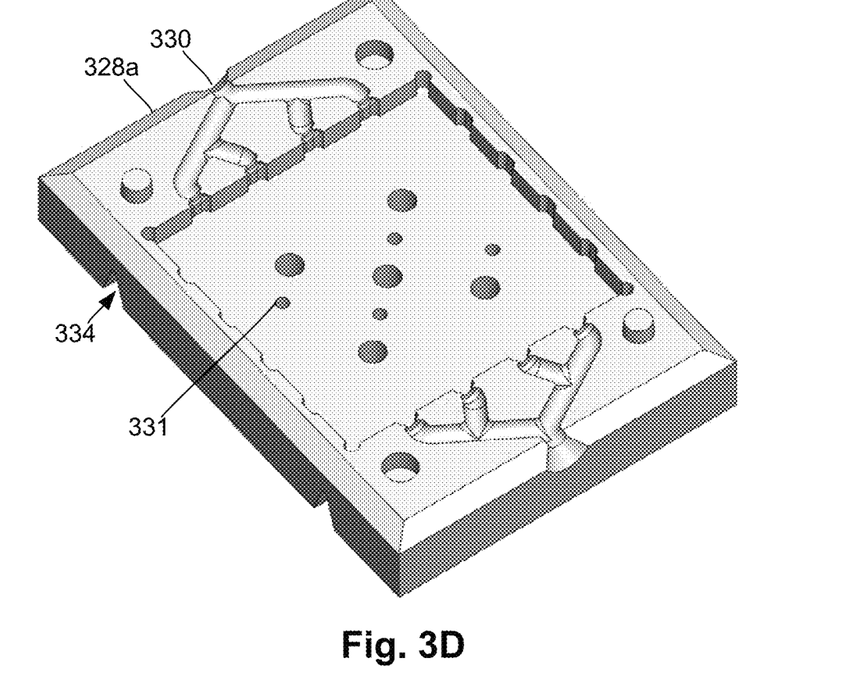
FIG. 3D is a schematic perspective view of one embodiment of a mold-half for forming an array of vapor cell elements/vapor cells, according to the invention.
Figure 3E:
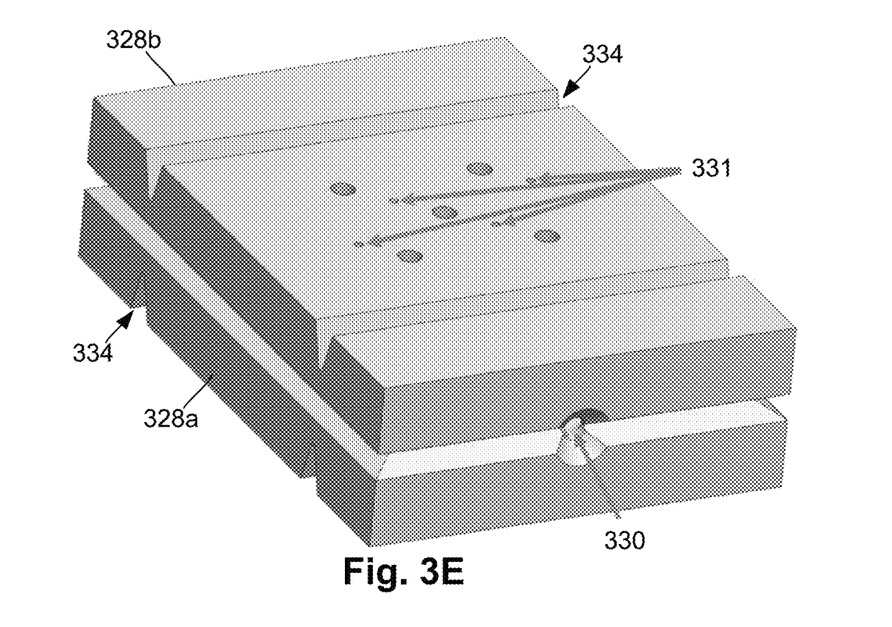
FIG. 3E is a schematic perspective view of one embodiment of a mold for forming an array of vapor cell elements/vapor cells, according to the invention.

After mounting to the alignment-maintaining film 326 using the alignment jig 322, the array of vapor cell elements 370 is then inserted into a mold 328 in step 408. FIG. 3D illustrates one embodiment of a mold half 328a and FIG. 3E illustrates one embodiment of the assembled mold 328 with injection port(s) 330 and venting ports 331. In at least some embodiments, the mold halves 328a, 382b are 3D-printed, or otherwise produced, using glass-filled photosensitive acrylic resin, or any other suitable polymer, for thermal and dimensional stability which can be beneficial properties during the heated curing process later during fabrication. In at least some embodiments, the mold halves 328a, 328b are conditioned with a mold release, such as a PTFE dry-film mold-release (for example, Sprayon MR311), to aid in removal after curing. In at least some embodiments, the treated mold halves 328a, 328b are subjected to a pre-bake before molding to increase effectiveness of the mold release coating.

With the vapor cell elements 370 disposed, inserted, or loaded in the mold 382, in step 410 the space between the vapor cell elements (including the spaces that were defined by the spacing features 324 of the alignment jig 322) is filled with a bonding material 332 (FIG. 3A) that is injected into the mold through the injection ports 330. Any suitable bonding material 332 can be used including, for example, epoxy, resin, thermoplastic material, or the like or any combination thereof. The bonding material 332 may be selected depending on the desired thermal and mechanical properties of the final mold-assembled array. For example, EPO-TEK T7109-19 thermally conductive epoxy may be suitable for mold-assembled arrays where a thermally homogenous mold-assembled vapor cell array with some flexibility is desired, while Loctite EA1C epoxy may be suitable for rigid mold-assembled arrays where the vapor cells are to be thermally isolated from each other.

Figure 3F:
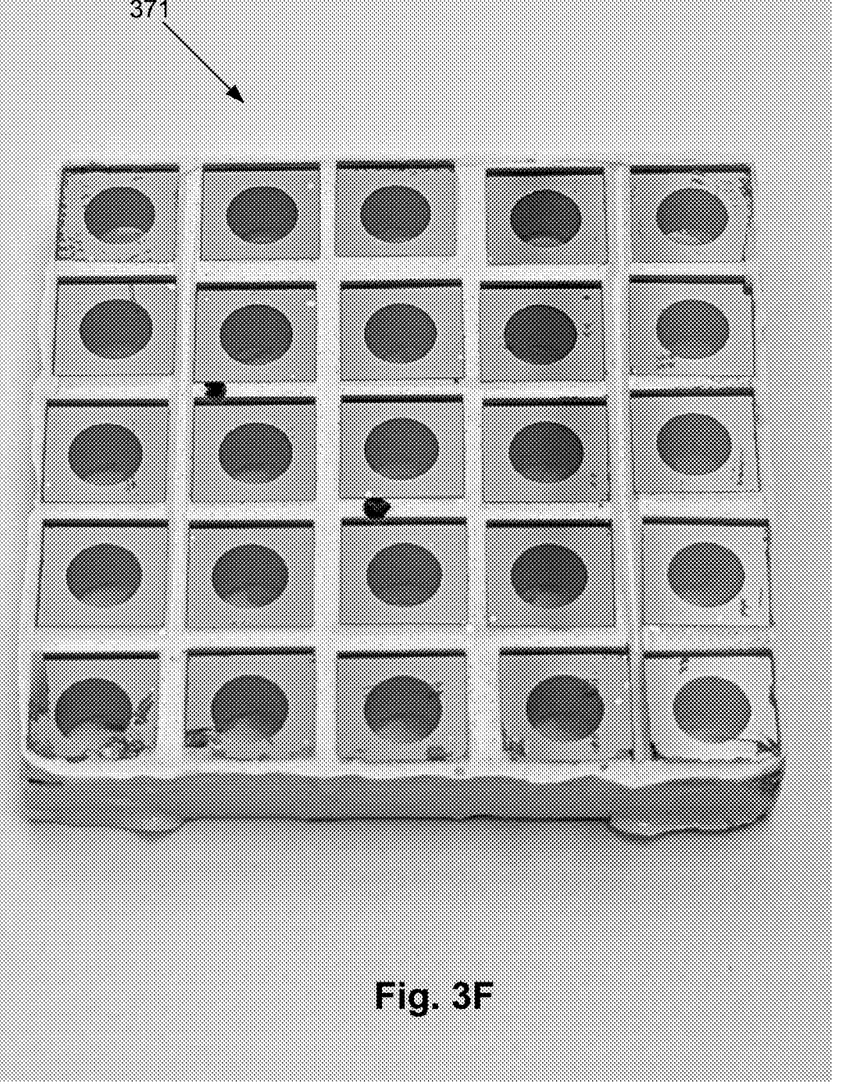
FIG. 3F is a photograph of one embodiment of an array vapor cell elements/vapor cells prior to post machining, according to the invention.

The selected bonding material 332 (epoxy or other bonding material 332) is injected (for example, side-injected) into the mold 328 and cured (for example, heat-cured or ultraviolet-cured.) When sufficiently cured, the mold-assembled vapor cell array is removed from the mold halves 328a, 328b in step 412. In at least some embodiments, this is aided by the incorporation of V-notches 334 on the mold halves 328a, 382b to cleanly break-away the side walls of the mold for better access to the part within. A vapor cell array assembly 371, prior to post-machining, is illustrated in FIG. 3F.

After mold removal, the alignment-maintaining film 326 on the optical faces of the vapor cell elements 370 is removed in step 414 and the vapor cell array assembly 371 can be post-machined to the final footprint. The optical faces of the vapor cell elements 370 are cleaned and the mold-assembled array's geometry is verified.

The aforementioned process can be utilized to fabricate any number of vapor cell elements 370 into a homogenous mold-assembled vapor cell array assembly 371. Additionally, though the previous description is for a square 5×5 array, the array is not limited to a square or rectangular geometry, and instead the final mold-assembled array assembly can be any desired geometry through modification of the pitch-setting alignment jig and mold halves.

Figure 5A:
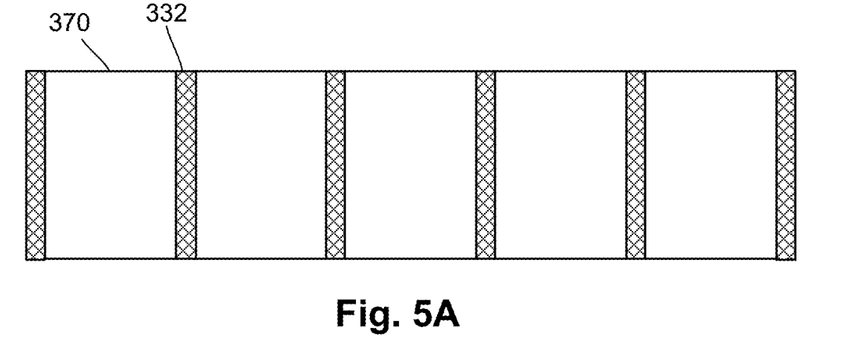
FIG. 5A is a cross-sectional view of the array of vapor cells of FIG. 3A, according to the invention.
Figure 5B:
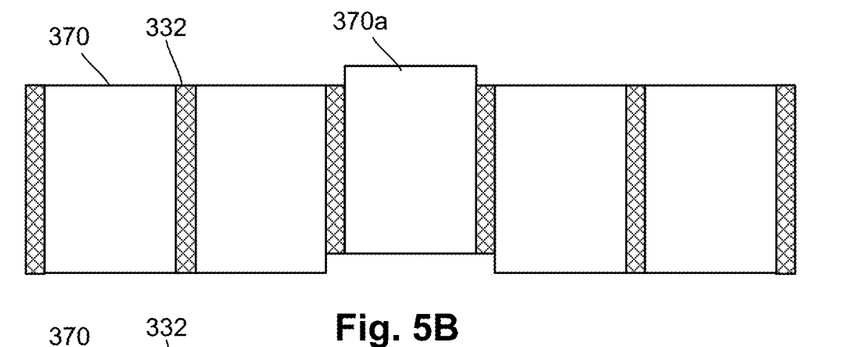
FIG. 5B is a cross-sectional view of another embodiment of an array of vapor cells with one vapor cell element/vapor cell raised relative to the rest, according to the invention.
Figure 5C:
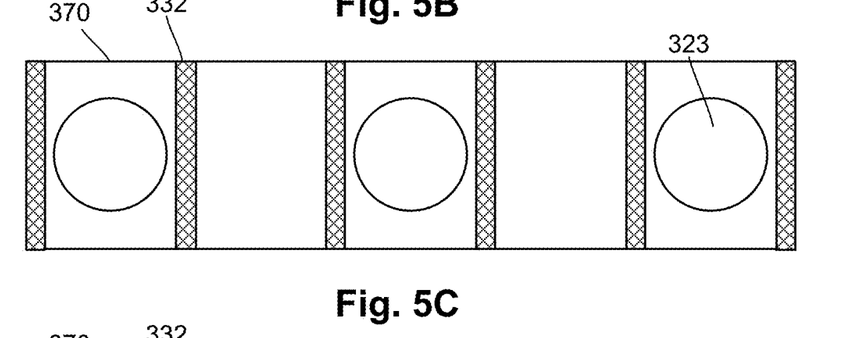
FIG. 5C is a side view of a third embodiment of an array of vapor cells with optical windows of some vapor cells oriented on the side surface, according to the invention.
Figure 5D:
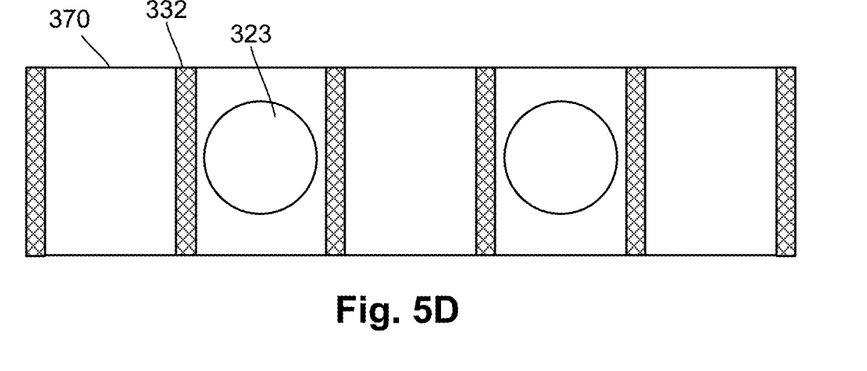
FIG. 5D is a top view of the third embodiment of an array of vapor cells with optical windows of some vapor cells oriented on the top surface, according to the invention.

In addition, to regular or irregular arrays, other features of the array can be altered or varied. FIG. 5A illustrates a cross-section of one row of the array 320 of vapor cell elements 370, with bonding material between 332, of FIG. 3A. In at least some embodiments, the selected arrangement includes different spacing between at least two pairs of adjacent vapor cell elements. In at least some embodiments, as illustrated in FIG. 5B, the selected arrangement includes at least one of the vapor cell elements 370a raised or lowered relative to an adjacent one of the vapor cell arrangements 370. In at least some embodiments, as illustrated in FIGS. 5C (side view of a row of vapor cell elements 370) and 5D (a top view of the same row of vapor cell elements 370) each of the vapor cells includes optical windows 323 and the selected arrangement includes at least one of the vapor cells having a differently orientated optical windows from another one of the vapor cells. In the illustrated arrangement of FIGS. 5C and 5D, three vapor cell elements 370 have optical windows 323 along a side surface and two vapor cell elements 370 have optical windows 323 along a top surface. Other features can be varied between vapor cells or vapor cell elements including, but not limited to, vapor cell size, vapor cell width or height or depth, distance between vapor cells, vapor cell internal cavity geometry, vapor cell optical window coating, or the like. Any of these variations can be combined together in any suitable combination.

In at least some embodiments, the vapor cells are produced so that the condensation of the alkali metal droplet 336 (FIG. 3C), from which the alkali metal vapor can be generated during operation of the magnetic field measurement system, is in a preferred location inside the vapor cell, so that the droplet does not need to migrate there across the optical beam aperture, which can interfere with operation. In at least some embodiments, the thermal properties of the assembled array 320 of vapor cells differ markedly from those of the individual vapor cells. For example, in at least some embodiments, the maximum droplet migration speed in a vapor cell array 320 may be much lower than the speed available to vapor cells, because the temperature gradient can be much greater in the single vapor cell configuration where all walls are accessible. Thus, in at least some embodiments, it is possible to drive condensation of the droplet at the single vapor cell level much more rapidly than after vapor cell array assembly.

In at least one embodiment, the individual vapor cells or vapor cell elements are heated anisotropically (for example, singly on a hot plate) in order to drive the alkali metal droplet 336 to a selected coldest internal surface. Once the droplet is substantially condensed there, the individual vapor cell elements 370 are assembled into the alignment jig 322 in the selected configuration with knowledge of the condensed droplet location in each vapor cell, so that the position of each droplet matches the cold spots that are to be created by an anisotropic heater during operation of the array of vapor cells in a magnetic field measurement system. For example, a square array of vapor cells may have a hottest zone at the center of the vapor cell array and a coldest zone at the perimeter of the vapor cell array; the droplets can be arranged to match this configuration before assembly of the vapor cell array so that they don't have to be migrated there after assembly.

By migrating, at relatively, high speed, the droplets within single cells to their final destinations, the droplets need only be maintained there by slight anisotropic heating of the array in order to keep the optical apertures clear of metal.

In at least some embodiments, applying a temperature gradient across the vapor cell array can yield gradients of alkali vapor density in different vapor cells. This is advantageous because it results in different levels of power broadening and different magnetic resonance widths. In at least some embodiments, variation of alkali vapor density in the vapor cell array can lead to different levels of optical power broadening. Cells with lower temperature may have greater levels of power broadening allowing operation in a larger range of magnetic fields. This can be particularly useful when searching for the magnitude and vector components of the ambient background magnetic field.

An alternative to use of a mold (and possibly an alignment jig) is the hand-applied cell-by-cell adhesion of cells using the bonding material 332 together into an array.

In at least some embodiments, the process can include one or more of the following features: the use of 3D-printed molds for epoxy molding; a break-away mold design to ease vapor cell array removal after curing; the creation of a single homogenous vapor cell array from individual vapor cell elements; the selection of a bonding material, such as epoxy, based on desired thermal properties of the final array assembly; the ability to change pitch and array layout without creating a new wafer; the ability to assemble vapor cells (originating from a top-down MEMS wafer production process) at non-perpendicular angles with respect to each other in the vapor cell array; the ability to create complex, non-rectangular vapor cell arrays; and the ability to condense an alkali metal droplet in preferred locations at the single vapor cell level, before assembly of the vapor cell array.

In at least some embodiments, the processes described herein can include one or more of the following advantages over conventional processes and vapor cell arrays: the ability to tailor thermal and mechanical properties of the vapor cell array, by selection of bonding material; the ability to modify vapor cell pitch and array layout, including array patterns that are not able to be diced without needing to fabricate and dice a new wafer; the preparation of multi-vapor cell systems with beam directions in some of the vapor cells that are aligned substantially angled or perpendicular to the top-down direction of some of the other vapor cells; and the ability to keep optical apertures clear of condensed alkali metal droplets by pre-condensing the alkali metal droplets in a selected location at the single-vapor cell level before assembly of the vapor cell array.

Another advantage of at least some embodiments described herein is the ability to ensure that all vapor cell elements are functional before selecting them for inclusion in the array which may improve performance and yields of the vapor cell arrays. Selecting vapor cell elements for matched properties can also benefit performance of the vapor cell arrays. For instance, in at least some embodiments, magnetometry vapor cell elements can be selected for uniformity of buffer gas pressure, leading to high uniformity of the optical resonance frequency. In at least some embodiments, this allows low-noise operation of the vapor cell array from a single laser source or more uniform operation parameters for an array of independent lasers matched to the array of vapor cells.

Examples of magnetic field measurement systems in which the embodiments presented above can be incorporated, and which present features that can be incorporated in the embodiments presented herein, are described in U.S. Patent Application Publications Nos. 2020/0072916; 2020/0056263; 2020/0025844; 2020/0057116; 2019/0391213; 2020/0088811; 2020/0057115; 2020/0109481; 2020/0123416; 2020/0191883; 2020/0241094; 2020/0256929; 2020/0309873; 2020/0334559; and 2020/0341081; U.S. patent application Ser. Nos. 16/884,672; 16/904,281; 16/922,898; 16/928,810; 16/984,720; 16/984,752; and Ser. No. 17/004,507, and U.S. Provisional Patent Applications Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; 62/983,406; 63/031,469; 63/037,407; 63/052,327; 63/058,616; 63/076,015; 63/076,880; 63/080,248; and 63/089,456, all of which are incorporated herein by reference.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A method of making an array of vapor cells for an array of magnetometers, the method comprising:
   providing a plurality of separate vapor cell elements, each vapor cell element comprising at least one vapor cell;
   arranging the vapor cell elements in an alignment jig to produce a selected arrangement of the vapor cells;
   attaching at least one alignment-maintaining film onto the vapor cell elements in the alignment jig;
   transferring the vapor cells elements and the at least one alignment-maintaining film from the alignment jig to a mold;
   injecting a bonding material into the mold and between the vapor cell elements to bond the vapor cell elements in the selected arrangement;
   removing the at least one alignment maintaining film from the vapor cell elements; and
   removing the bonded vapor cells elements in the selected arrangement from the mold to provide the array of vapor cells.

2. The method of claim 1, wherein at least one of the vapor cell elements comprises multiple vapor cells.

3. The method of claim 1, wherein the alignment jig comprises a plurality of spacing features to separate the vapor cell elements in the selected arrangement.

4. The method of claim 3, wherein each of the spacing features provides a same separation distance between the vapor cell elements separated by the spacing features.

5. The method of claim 3, wherein at least two of the spacing features provide a different separation distance between the vapor cell elements separated by those spacing features.

6. The method of claim 3, wherein the spacing features comprise partially drafted faces to facilitate insertion of the vapor cell elements.

7. The method of claim 3, wherein the spacing features have a width that is thinner than a final separation distance between the vapor cell elements separated by the spacing features.

8. The method of claim 1, wherein attaching the at least one alignment-maintaining film comprises attaching a first alignment-maintaining film onto the vapor cell elements in the alignment jig and then attaching a second alignment-maintaining film on an opposite side of the vapor cell elements from the first alignment-maintaining film.

9. The method of claim 8, further comprising removing the vapor cell elements from the alignment jig prior to attaching the second alignment-maintaining film.

10. The method of claim 1, wherein the bonding material is epoxy.

11. The method of claim 1, wherein the bonding material is a thermally conductive epoxy.

12. The method of claim 1, wherein the bonding material is a flexible epoxy.

13. The method of claim 1, wherein the selected arrangement comprises different spacing between at least two pairs of adjacent vapor cell elements.

14. The method of claim 1, wherein the selected arrangement comprises an irregular arrangement of the vapor cell elements.

15. The method of claim 1, wherein the selected arrangement comprises at least one of the vapor cell elements raised or lowered relative to an adjacent one of the vapor cell elements.

16. The method of claim 1, wherein the selected arrangement comprises at least one of the vapor cells having a different size from another one of the vapor cells.

17. The method of claim 1, wherein each of the vapor cells comprises optical windows, wherein the selected arrangement comprises at least one of the vapor cells having a different orientation of the optical windows from another one of the vapor cells.

18. The method of claim 1, further comprising locating an alkali metal droplet in a specified location in each of the vapor cells.

19. The method of claim 18, wherein locating the alkali metal droplet comprises controlling a temperature of the array of vapor cells to locate the alkali metal droplets in the specified locations.

20. The method of claim 19, wherein controlling the temperature comprises applying a temperature gradient to the array of vapor cells to locate the alkali metal droplets in the specified locations.

* * * * *